United States Patent [19]

Stockel

[11] Patent Number: 4,506,628
[45] Date of Patent: Mar. 26, 1985

[54] ANIMAL LITTER

[76] Inventor: Richard F. Stockel, 475 Rolling Hills Rd., Bridgewater, N.J. 08807

[21] Appl. No.: 513,178

[22] Filed: Jul. 13, 1983

[51] Int. Cl.³ .............................................. A01K 1/015
[52] U.S. Cl. .................................................... 119/1
[58] Field of Search ............................ 119/1; 424/357

[56] References Cited

U.S. PATENT DOCUMENTS

| | | | |
|---|---|---|---|
| 2,728,732 | 12/1955 | Arnett, Jr. et al. | 252/383 |
| 4,048,337 | 9/1977 | Fabbian | 424/357 |
| 4,129,094 | 12/1978 | Stockel | 119/1 |
| 4,275,684 | 6/1981 | Kramer et al. | 119/1 |

Primary Examiner—Robert P. Swiatek

[57] ABSTRACT

An improved and novel animal litter is described utilizing alumina, aluminosilicates or coal residues as the substrate intimately mixed with monomers containing acid functionalities which are polymerized in-situ. The resulting mixture is then extruded into pellets of any size or shape. Animal litter pellets prepared by this invention have vastly improved water adsorption properties, deodorizing capacity, and they do not have to be cured at high temperatures.

22 Claims, No Drawings

ANIMAL LITTER

INTRODUCTION

In the past, many attempts have been made to replace Fuller's earth as an animal litter. Fuller's earth is mostly composed of two minerals, attagulgite and montmorillonite, which makes up about 90% by weight. The more active Fuller's earth develops 60-70% porosity on surface areas of 120-140 $m^2/g$. Pores have mean equivalent diameters of 170-200 Å. It can take up to 30-80% of its weight without losing the apparent dryness. Clays are basically built up from layer lattice structures stacked parallel to each other in sandwich fashion. Fuller's earth is chemically an aluminum magnesium oxide silicate. While other adsorbents have tried to replace Fuller's earth from the animal litter market, they have all failed, probably due to the fact that nothing as cheap as Fuller's earth can do a better job for this end use. It should also be recognized that Fuller's earth does not have deodorizing capability. This may be due to the relatively small pore size of the particles and/or the fact that no catalytic sites containing active metal oxides are available. Large organic type metabolic decomposition products are not effectively adsorbed into Fuller's earth, although the ammonium ion can be accomodated. Therefore, most of the potential malodorous materials are weakly adsorbed on the surface and will evaporate upon prolong standing.

The need for an effective adsorbing and deodorizing animal litter is quite apparent from the patent literature where a number of attempts have been made to improve or replace Fuller's earth. The in-situ formation of aluminum sulfate by the reaction of alumino silicates with sulfuric acid, coupled with the use of an onium compound as a germicide, is taught in U.S. Pat. No. 2,895,873. Similar claims are made in U.S. Pat. No. 3,029,783. The concept of controlled release of a pleasant fragrance when a clay material is moisturized by urine or fecal material is described in U.S. Pat. No. 3,675,625. Other deodorizing materials such as chlorophyl, sodium dihydrogen phosphate, potassium dihydrogen phosphate, potassium acid phthalate or a combination of these in conjunction with Fuller's earth is described in U.S. Pat. No. 3,735,734. Ferrous sulfate heptahydrate is described as the active ingredient in deodorizing animal litter in U.S. Pat. No. 3,776,188. In this patent, the litter material is either fly ash, a zeolite or combination thereof. An animal litter prepared from a mixture of alfalfa, bentonite and a binder for adsorbing and neutralizing the odors of animal waste matter is described in U.S. Pat. No. 3,789,797. Another slow release of a fragrance from adsorbent cellulosic and/or aluminosilicate materials is described in U.S. Pat. No. 3,921,581. Water soluble or water swellable polymers which can release a fragrance when exposed to moisture containing malodorous substances are useful in animal litters, U.S. Pat. No. 4,009,684.

In addition to clays, both natural or synthetic, a number of organic type waste products have been claimed to be effective animal litters. Acid buffered cellulosic materials have been claimed in U.S. Pat. No. 3,059,615 as an animal litter in deodorizing obnoxious odors. Dehydrated alfalfa is claimed to have deodorizing capabilities as claimed in U.S. Pat. No. 3,286,691. A slight deviation from the use of alfalfa is a mixture of alfalfa with perlite or vermiculite as claimed in U.S. Pat. No. 3,425,397. Camphane derivatives have also been claimed, U.S. Pat. No. 3,636,927, to have unusually effective masking ability towards odors when used in either inorganic or organic type animal litters. Many other types of organic materials have also been claimed, for example, foamed plastics containing deodorizers as described in U.S. Pat. No. 3,765,371. Cherry pit extract is claimed in U.S. Pat. No. 3,816,577 as an effective deodorizer used in animal litter. An improved pet litter, as claimed in U.S. Pat. No. 3,821,346 teaches the use of recycled mollases serum. Another adsorbing organic substance useful as an animal litter excrement control system involves the use of popcorn by itself or with mixtures of clay or alfalfa is delineated in U.S. Pat. No. 3,916,831. Other organic waste materials like peanut hulls containing sodium bicarbonate is described in U.S. Pat. No. 3,983,842. U.S. Pat. No. 4,129,094 teaches the use of fly ash, bottom ash or boiler slag, which exhibit adsorbing and deodorizing properties when used as a cat litter either alone or in a mixture containing Fuller's earth.

INVENTION

It is therefore the object of this invention to provide an improved animal litter and particularly, a cat litter composition. It is another object of this invention to provide an animal litter which is highly adsorbent and an excellent deodorizer. A further object of this invention is to provide such improved animal litter compositions from inexpensive and readily available raw materials. It is yet another object of this invention to provide an animal litter composition which is more economical to produce than Fuller's earth or other available animal litter compositions. The foregoing and other objects of this invention will be more readily comprehended from the following detailed description of the invention.

DETAILED DESCRIPTION OF THE INVENTION

While other materials such as alumina or aluminosilicates materials can be used in this invention, the preferred adsorbent/deodorizing compositions or choice are coal residues, e.g. fly ash, bottom ash or boiler slag. This preference is primarily due to the abundance and very low costs. In fact most often coal residues are given away free by electrical generating stations. The appearance of this coal residue ranges from a gray-white to a dark black color, while the particle size can range from a very fine spherical material like fly ash to a much coarser and larger type material, spherical in nature, bottom and boiler slag. All of these coal residues are high in silica, alumina, alkali and alkaline ion oxides as well as ferric oxide. These materials are readily found throughout the United States, wherever coal is burned as a source of power for a public utility or a manufacturing facility. Currently there are over 500 utilities burning coal throughout the United States resulting in 80 billion pounds of fly ash, 120 billion pounds of bottom ash and boiler slag.

The percent composition of fly ash ranges according to the following:

| | |
|---|---|
| silica | 34–35% by wt. |
| alumina | 15–30% by wt. |
| ferric oxide | 12–22% by wt. |
| calcium oxide | 2–7% by wt. |
| magnesium oxide | 0.5–1.0% by wt. |

| | Fly Ash/Bottom Ash/ Boiler Slag | Fuller's earth |
|---|---|---|
| sodium and potassium oxides | 1.5–4.0% by wt. | |

Bottom ash and boiler slag have similar compositions.

The following table lists the relative advantages of fly ash, bottom ash or boiler slag versus Fuller's earth.

| | Fly Ash/Bottom Ash/ Boiler Slag | Fuller's earth |
|---|---|---|
| Adsorption | + | + |
| Availability | + | |
| Cheaper costs | + | |
| Deodorizing ability | + | |
| Toxicity | + | + |
| Animal acceptance | + | + |
| Longer lasting | + | |
| $NH_3$ adsorption | + | |

Before using finely divided fly ash as an animal litter, it is necessary to pelletize it with a suitable binder, U.S. Pat. No. 4,374,743 describes such a binder which is sodium silicate having a specific silica/sodium oxide range. Even though the teachings of U.S. Pat. No. 4,374,743 enhance the state of the art in pelletizing coal residues, this present technology pelletizes coal residues conferring properties which were unattainable by any known method prior to this invention.

There are three basic areas which require additional improvement in order to produce a superior animal litter over the present state of the art. These are: 1. higher water adsorption; 2. better deodorizing ability, particularly for ammonia and volatile amines; 3. the elimination of the energy requirement in the pelletizing step and yet achievement of the necessary compression strength required for the application.

One approach to solving this problem which was explored previously in U.S. Pat. No. 4,129,094 was the use of hydrophilic polymers as binding agents for coal residue in forming shaped particles thereof. Using the teachings of this invention gave a slight improvement in adsorption characteristics. However, the introduction of a high molecular weight polymer mixed with a coal residue resulted in any mechanical and impractical problems. When performing this mixing operation it was very difficult to assure that the polymeric compound was being evenly dispersed in the coal residue and this was coupled with the difficulty of extruding the mixture.

This present invention has much greater applicability than for just coal residues, for example, alumina or aluminosilicate can be treated in the same manner. Thus, coal residues, alumina and aluminosilicates can be made into superior performing animal litters by the teachings of this invention. The compositions of this invention are prepared by the in-situ polymerization of a vinyl or allyl monomer or combinations thereof, containing acidic pendant functionalities. By intimate mixing of any of the substrate material described previously with water and an appropriate monomer or monomers containing a catalyst system, a viscous mixture with excellent initial green strength can be extruded into pellets. After polymerization is complete, a pellet with superior properties is obtained. The final pellet has sufficient compression strength, high water adsorption, increased ammonia and amine affinity and does not require an energy intense step in its preparation.

The vinyl or allyl monomer or monomers containing an acidic function can be a derivative containing a carboxylic, sulfonic, phosphonus, phosphonic group(s) or any combination of these. Further, the monomer can be monofunctional, difunctional or multifunctional acid containing monomers.

Copolymers or terpolymers containing acid groupings with non-acid functionalities can be employed as well in this invention. However, the novel properties of animal litter prepared by this invention are primarily a result of the acid functionalities. Anyone skilled in the art of polymer chemistry can prepare random, graft, block or interpenetrating network polymers useful for this invention, however in every case the polymer system must contain an acidic functionality in order to carry out the teachings of this invention.

U.S. Pat. No. 4,129,094 points out the use of natural or synthetically derived hydrophilic polymers as well as inorganic materials are binding agents for coal residues. This patent does not teach the in-situ polymerization of a hydrophilic polymer or copolymer, nor does it specifically suggest polymers containing carboxylic, sulfonic, phosphorus or phosphonic functionalities. In fact, the suggested polymers of U.S. Pat. No. 4,129,094 would not result, if these were used, in an animal litter having properties as that attained by the teachings of this present invention.

The resulting pelletized animal litter, as practiced by this invention, has vastly improved properties such as higher water adsorption, sufficient compression strength without a high temperature cure, higher affinity in complexing with ammonia or amines and a low or non-existent cure step to make the shaped pellet animal litter. These advantages represent a significant improvement over commercially available products.

Representative examples of carboxylic containing monomers are acrylic acid, methacrylic acid, itaconic acid, maleic acid, allyl carboxylic acid, styrene carboxylic acid and similar type compounds. Representative examples of sulfonic containing monomers are ethylenesulfonic acid, allylsulfonic acid, styrenesulfonic acid, 2-sulfoethylmethaerylate, N-acryloyl taurine and many similar type compounds. Some examples of phosphorus acid monomers are vinyl phosphonic acid, allyl phosphonic acid, phosphonous and phosphonic derivatives of styrene and similar type compounds. Anyone skilled in the art could find additional examples of monomers having acidic pendant groups in the published literature but the results would be the same as the teachings of this invention.

The following examples set forth are not a limitation of the invention but instead the broad applicability of this finding is intended to be the teachings of this invention. These experiments are meant to be illustrative of the spirit of this invention.

EXAMPLE 1

To 90 g of fly ash was added 30–40 g of water (enough to form a pliable dough-like substance) containing 10 g of acrylic acid, 0.30 g $NaHSO_3$ and 0.2 g $K_2S_2O_8$. The mixture was extruded into pellets and within 15–20 minutes, polymerization is near complete and pellets having properties useful as an animal litter are obtained.

EXAMPLE 2

The same procedure as example 1 was used, except that catalyst system was comprised of only 0.3 g of $K_2S_2O_8$. In this example the non-polymerized mixture had sufficient green strength and was extruded into pellets which fell into a mineral oil bath of 85° C. temperature. Within 1 hour the pellets were cured and had similar properties as the pellets prepared in Example 1.

EXAMPLE 3

To 90 g of an aluminosilicate powder was added 10 g of vinyl sulfonic acid and approximately 25 g of water containing 0.3 g $K_2S_2O_8$ and 0.35 g $NaHSO_3$. This mixture was mixed thoroughly and extruded into pellets and within ½ hour the polymerization was completed. The pellets thus prepared had the desirable properties required of an animal litter product.

EXAMPLE 4

To 90 g of alumina was added enough water to form a pliable dough which was intimately mixed with 15 g of vinyl phosphonic acid containing the redox catalyst as described in Example 1. This mixture was extruded into pellets and within 40 minutes polymerization appeared completed. The properties of these pellets functioned equally well as those prepared in Examples 1, 2 or 3.

EXAMPLE 5

To 90 g of bottom ash was added enough water to give a dough-like substance and to this was added 10 g of acrylic acid and 5 g of vinyl sulfonic acid containing the same redox catalyst system described in Example 1. Pellets were extruded which hardened within 30 minutes and a product having useful properties as an animal litter was obtained.

It is obvious from these examples that acid functionalities, e.g. carboxylic, sulfonic, phosphinic and phosphonic and other acidic pendant groups on monomers polymerized in-situ within the carrier substrate via redox or thermal methods causes an agglomeration, which then can be easily pelletized. The animal litter pellets have outstanding properties resulting in a superior product.

These polymerized monomers form an effective binder with the acidic group complexing with the many multi valent cations present in the mixture. The polymer itself also acts as a binder, however, other hydrophilic polymers without an acid group do not function nearly as well. The compression strength and the odor adsorbing properties would be unacceptable as an effective animal litter.

Experimentally about 5% by weight of the binding agent as described in this invention is about the lower limit to prepare an effective animal litter. Considering costs and other practical potential problems, the maximum weight percent was found to be about 40%.

The following examples will serve to illustrate the effectiveness of the invention's teachings whereby a monomer containing an acid functionality is polymerized in-situ intimately mixed with a coal residue, aluminosilicate or alumina. These examples are illustrative and do not limit the scope of this invention.

EXAMPLE 6

Fuller's earth and a fly ash (as prepared in Example 1) were tested as a cat litter and their relative effectiveness compared in this example. In these experiments, 10 full cups of the litter material were added to 18×24×4 inch cat boxes and two tests were conducted separately on two cats; one male, the other female, using each of the two litter compositions.

In the case of Fuller's earth, the litter lasted an averge of 139 hours, however, when the cats used the cat box after this period, the litter became lumpy and the odor eminating from the cat's excrement became excessive, indicating that Fuller's earth was no longer effective.

When the cat litter from Example 1 (fly ash) was used, the litter remained odor free even when the litter was changed after 235 hours since it became slightly lumpy and the cats were not receptive to using the cat box.

EXAMPLE 7

The test procedure in this example was similar to Example 6 except that one male cat was tested and that 7 cups full of litter were used in each experiment. In the case of Fuller's earth, an aluminosilicate mineral, the odor eminating from the cat excrement was excessive and the litter lasted for approximately 10 days and 4 hours. When a mixture of Fuller's earth treated in a similar fashion to Example 2, the litter laster for 14 days and was odor free and not lumpy like the untreated Fuller's earth.

The results of these two experiments clearly demonstrate the remarkable properties conferred on these adsorbing materials by polymerizing monomers containing acid groups in an intimate fashion as compared to an untreated control sample. These results clearly delineate the enhanced water adsorption and deodorizing ability of this invention.

I claim:

1. An animal litter composition being selected from a group consisting of coal residue, alumina, aluminosilicate and mixtures thereof, said composition mixed and polymerized in-situ with a monomer or monomers containing at least one acidic functional group present in the molecule.

2. An animal litter composition as described in claim 1 where said coal residue is fly ash, bottom ash or boiler slag.

3. An animal litter composition as described in claim 1 where said aluminosilicate is a natural occurring mineral.

4. An animal litter composition as described in claim 1 where said aluminosilicate is synthetically derived.

5. An animal litter composition as described in claim 1 where said monomer or monomers comprise from about 5% to about 40% by weight of the total weight of the animal litter.

6. An animal litter composition as described in claim 5 where said monomer or monomers contain at least one carboxylic functionality.

7. An animal litter composition as described in claim 5 where said monomer or monomers contain at least one sulfonic functionality.

8. An animal litter composition as described in claim 5 where said monomer or monomers contain at least one phosphinic functionality.

9. An animal litter composition as described in claim 5 where said monomer or monomers contain at least one phosphonic functionality.

10. An animal litter composition as described in claim 5 whereby the monomer or monomers are polymerized by redox free radical initiators.

11. An animal litter composition as described in claim 5 whereby the monomer or monomers are polymerized by thermally initiated free radical initiators.

12. An animal litter composition as described in claim 5 containing at least one acidic functional group in at least 50% of the total weight of monomers.

13. A process for preparing animal litter comprising: mixing one material from a group consisting of a coal residue or an aluminosilicate mineral with a monomer or monomers containing functional acidic groups; adding water and a free radical initiator; polymerizing said monomer or monomers; pelletizing the resulting polymerized mixture; and subjecting the pellets to a drying step.

14. A process for preparing an animal litter as described in claim 13 whereby the coal residue is fly ash, bottom ash or boiler slag.

15. A process for preparing an animal litter as described in claim 13 whereby the aluminosilicate is a natural occurring mineral.

16. A process for preparing an animal litter as described in claim 13 whereby the aluminosilicate is synthetically derived.

17. A process for preparing an animal litter as described in claim 13 where said monomer or monomers comprise from about 5 to about 40% by weight of the litter.

18. A process for preparing an animal litter as described in claim 13 where said monomer or monomers contain at least one carboxylic functionality.

19. A process for preparing an animal litter as described in claim 13 where said monomer or monomers contain at least one sulfonic acid functionality.

20. A process for preparing an animal litter as described in claim 13 where said monomer or monomers contain at least one phosphinic acid functionality.

21. A process for preparing an animal litter as described in claim 13 where said monomer or monomers contain at least one phosphonic acid functionality.

22. A process for preparing an animal litter as described in claim 13 where said mixture is extruded into pellets of a size suitable as an animal litter.

* * * * *